United States Patent [19]

Kraskin

[11] 3,935,862

[45] Feb. 3, 1976

[54] INHIBITION OF CONDITIONS ARISING FROM MICROBIAL PRODUCTION OF AMMONIA

[75] Inventor: Kenneth S. Kraskin, Milltown, N.J.

[73] Assignee: Personal Products Company, Milltown, N.J.

[22] Filed: June 12, 1974

[21] Appl. No.: 478,663

[52] U.S. Cl. .................. 128/287; 128/284; 424/319
[51] Int. Cl.² .......................................... A61F 13/16
[58] Field of Search ............... 128/284, 287, 290 R; 424/27, 28, 319, 359

[56] References Cited
UNITED STATES PATENTS

| | | | |
|---|---|---|---|
| 2,837,462 | 6/1958 | Morin | 128/290 R |
| 3,004,895 | 10/1961 | Schwartz | 128/287 X |
| 3,061,512 | 10/1962 | Anderson, Jr. et al. | 424/319 |
| 3,198,828 | 8/1965 | Matter | 424/27 |
| 3,340,875 | 9/1967 | Dudley et al. | 128/290 R |
| 3,490,454 | 1/1970 | Goldfarb et al. | 128/290 R |
| 3,707,148 | 12/1972 | Bryce | 128/284 |
| 3,804,092 | 4/1974 | Tune | 128/284 |

*Primary Examiner*—Aldrich F. Medbery

[57] ABSTRACT

Methods, compositions and products are described which inhibit the development of undesirable conditions arising as a result of microbial formation of ammonia from urea in excreted urine. Amino acid compounds are employed.

1 Claim, No Drawings

INHIBITION OF CONDITIONS ARISING FROM MICROBIAL PRODUCTION OF AMMONIA

This invention relates to methods, compositions and articles of manufacture useful for inhibiting inflammation, malodor and other ammonia caused problems in human hygiene.

Inflammation of the skin in the pelvic area in diaper-wearing infants is well-known. This inflammatory disorder called "diaper rash", is primarily caused by ammonia which is at least partially formed through bacterial decomposition of the urea present in urine and the retention of the ammonia so formed in close proximity to the pelvic area by the diaper as well as by other articles such as clothing, bed sheets, etc. Frequent changes and use of powders have not completely solved the problem. Contact of the skin with the urine soaked diaper and other articles cannot be avoided entirely. Moreover, prolonged periods of contact frequently cannot be avoided, such as during the night. A similar problem exists with incontinent patients and incontinence pads. Thus, it is desirable that there be found a method for preventing the formation of ammonia in the diaper, pads and other articles.

Urine has been reported to contain 2% urea and about 0.5% normal metabolic ammonia. (West & Todd, Textbook of Bio-chemistry, Mac Millian, N.Y., 1957). Thus, although ammonia is present in minor amounts in the human urine as a normal metabolic product, a potentially large amount of ammonia can be formed by microbial action on the excreted urea.

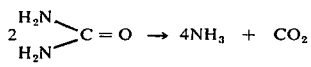

It can be seen that from each molecule of urea, two molecules of ammonia are formed. Non-pathogenic microorganisms such as the intestinal microorganisms, Proteus and Klebsiella species, and soil-borne microorganisms Bacilli and Sarcina are known to act on urea to produce ammonia.

If the conversion of urea to ammonia can be inhibited, undesirable conditions such as the inflammatory disorders in infants and incontinent patients may be avoided or minimized. Moreover, undesirable odors may be minimized. However, the means must be such that harmful or undesirable effects are not produced by the agent employed. Further, the means should be such that it is readily adaptable to current methods of infant or patient care. Moreover, it is highly desirable that the results be accomplished without kill of the non-pathogenic microbial flora. As is well-known, the kill of the non-pathogens invites invasion by opportunist organisms such as pathogenic bacteria, fungi or yeast whose presence may become manifest in dermatitic, febrile, inflammatory or other undesirable responses.

It has been discovered that the development of undesirable conditions arising as a result of microbial formation of ammonia from urea in excreted urine may be inhibited by introducing to the situs of ammonia formation, an inhibitory amount of an amino acid compound.

The expression, "situs of ammonia formation" refers to the loci where urine is retained. Various loci may serve such function. Thus, ammonia formation may occur on skin surfaces surrounding the area of urinary discharge. It may further occur on devices intended to receive urine such as diapers, incontinence pads, bed pads, etc. This result may be accomplished by administering an amino acid compound in a topical carrier to the pelvic area or by incorporating in a diaper, diaper liner, incontinence pads, bed pads, etc. as carrier. Thus, it is readily accomplished by existing means of infant and patient care. Moreover, the inhibition of ammonia product is accomplished by such minor amounts that undesirable side reactions such as alteration of microbial flora or injury to the infant or patient is avoided.

Amino acid compounds useful for the practice of the present invention generally have in the structure at least one arrangement of the amino group to acid group as follows:

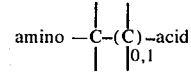

The acid group is preferably carboxylic, —COOH, but may be sulfonic, —SO$_2$OH, or phosphonic, —PO(OH)$_2$. The amino may be substituted and the carbon chain may contain groups such as hydroxyl, —OH, sulfhydryl, —SH, and ether —O—.

An important group of compounds which inhibits the formation of ammonia are the aminopolycarboxylic acid compounds. By "aminopolycarboxylic acid compound" is meant a compound in which the amino nitrogen has attached thereto two or more substituent groups of the general structure:

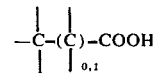

and includes those having more than one amino group. It also includes water soluble salts. Preferred salts are monovalent salts such as sodium and potassium salts. The best known compounds of this class are the acids and salts of ethylenediaminetetraacetic (EDTA) acid, diethylenetri-aminepentaacetic (DTPA) acid and N-hydroxyethylethylenediaminetriacetic (HEDTA) acid. These compounds are available commercially through trade names such as VERSENE, VERSENEX and VERSENOL, SEQUESTRENE, etc. Other typical compounds in this class include triethylenetetraaminehexacetic acid, 1,2-diaminocyclohexane-N,N'-tetraacetic acid, dihydroxyethylethylene-diaminediacetic acid, iminodiacetic acid, hydroxyethyliminodiacetic acid and nitrilotriacetic acid and their salts as well as propionic acid analogs.

Amino acid compounds of other classes include hydroxyalkylamino acids, sulfhydryl amino acids, aminosulfonic acids, aminophosphonic acid compounds and ether amino acids such as methoxyethyliminodiacetic acid, ethylene-bis-(oxypropylaminodiacetic acid), ethylene-bis-(oxyethyliminodiacetic acid), aminomethyl phosphonic acid (N,N- diacetic acid), aminoethyl-N-methyliminodiacetic acid, ethylenediaminetetra(methylene phosphonic acid), cysteine, β-mercaptoethyliminodiacetic acid, β-methylmercaptoethyliminodiacetic acid, etc.

The amino acid compound is believed to be proceeding by removal of the necessary metallic co-factor for the enzymatic production of ammonia. However, the invention is not limited to any particular theory and the preventative control of ammonia production may be achieved without detrimental effect on normal microbial flora.

The effectiveness of the amino acid compound in the control of microbial ammonia production may be illustrated in the following example:

A 25 milliliter sample of urea broth inoculated with Proteus sp., a second 25 milliliter sample similarly inoculated and further containing 0.2% by weight of disodium ethylenediaminetetraacetate and an uninoculated control were incubated at 37°C. for 24 hours and thereafter determined for presence of ammonia. The determination was carried out on 10 milliliter samples by the method of standard ammonia reagent additions at pH 12 employing an ammonia electrode with alizarin yellow indicator and determining the change in electrode potential on addition of a known concentration of ammonium ions. (Orion Research, Inc., Instruction Manual, Ammonia Electrode Model 95-10).

The results were as follows:

| Sample | % $NH_3$ |
| --- | --- |
| Control Broth | 0.057 |
|  | 0.049 |
| Proteus Inoculated | 1.14 |
| Broth | 1.11 |
| Proteus Inoculated | 0.19 |
| Broth with 0.2%$Na_2$EDTA | 0.19 |

The amino acid compounds are used in such amounts as to give a final concentration of at least 0.01% by weight of excreted urine. The upper limit is dictated by practical considerations. Generally speaking, adequate inhibition is obtained at levels of about 0.5%. No advantage is seen in employing amounts in excess of 5% by weight of excreted urine.

The exact amount to be incorporated in a composition or article of manufacture depends on the method of use. Thus, the amounts employed for topical application such as in a lotion or powder may differ from the amount which would be incorporated in a disposable diaper. Only such amounts in excess of the desired final concentration to compensate for the expected or possible dilution effect at the ultimate situs are usefully employed. Generally, at least about 0.5% by weight of the amino acid compound is incorporated in the carrier. However, the amount is also dependent on the amino acid compound. Thus, a smaller amount of tetrasodium ethylenediaminetetraacetate appears to achieve a similar degree of control as a larger amount of disodium ethylenediaminetetraacetate. Where the contact is likely to be directly on the skin, it is preferred that the amino acid compound be in a form which is near the neutral pH range.

In its use, the amino acid compound is conveniently applied to diapers. It is especially adaptable for incorporation in disposable diapers at the time of manufacture. Conventional disposable diapers usually contain a thin, water-permeable facing (liner) sheet covering the interior side of the diaper, viz., the side which is to contact the skin in use, and a thin (usually moisture-impermeable) backing sheet covering the exterior side of the diaper, remote from the skin, with the porous, highly absorbent core (pad) being located between the interior and exterior facing (liner) sheets. The cores are conventionally made of layers of fibers such as carded cotton webs, air-layered cellulosic fiber webs, comminuted wood pulp battings, tissue pulp or like materials but may be made of newer synthetic materials such as synthetic polymer foams and fibers.

By application of the amino acid compound to the surface of the cores of the disposable diapers or to the fibers in the covers of the diapers or both, novel products are provided which are useful for inhibiting inflammation, malodor and other ammonia caused problems. In these novel diapers, the amino acid compound is present on the surface thereof in an amount ranging from about 0.001 gm. per square inch to about 0.5 gm. per square inch. Most preferred is an amino acid compound concentration of about 0.05 gm. per square inch, although higher amounts may be employed.

The amino acid compound may be applied to the diapers by any known method for applying materials thereto, such as by spraying in an aqueous spray, a solvent spray or an aerosol spray of mist or powder. An aerosol spray may employ such propellants as dichlorodifluoromethane, dichlorotetrafluoroethane, etc.; a solvent spray may employ substantially inert solvents such as isopropanol. The use of a propellant or inert organic solvent is preferred over an aqueous solution or suspension inasmuch as the latter requires more extensive drying subsequent to application of the amino acid compound.

Additionally, the amino acid compound may be applied in a similar manner to diaper liners for use with fabric diapers, to protective bed padding, etc.

In another aspect of the present invention, the amino acid compound may be incorporated into vehicles suitable for topical application such as powder, lotion, cream, aerosol, etc. to provide novel compositions which may be applied to skin at the time of diaper change. In this way, the amino acid compound present on the dermal surface in the area likely to come in contact with the urine acts to inhibit conversion of urea to ammonia by microbial enzymes. Moreover, if incorporated into powder, the powders may be applied to conventional diapers at time of diaper change.

When the novel composition is an emollient composition, i.e., lotion or cream, with or without propellant, the amino acid compound is added in an amount of at least about 2% by weight of the total weight of the composition. The amount may be as high as 10% but is not limited thereto. When the novel composition is a powder, the amino acid compound is added in an amount of at least about 0.01%. The upper limit is dictated by practical considerations. No advantage is seen in including amounts over about 10% by weight of the amino acid compound.

When incorporation is to be made into lotion, cream or aerosol, the amino acid compound may be added in a solvent compatible with the system in which it is incorporated such as water, glycerol, propylene glycol, tripropylene glycol methyl ether, ethanol, etc. Alternatively, the amino acid compound may be added to the final composition and intimately admixed therewith. Such would be the preferred method for preparing dusting powders. Carrier materials include ointment additives such as polysorbate 80, polyoxyethylene sorbitan trioleate; surfactants and emulsifiers such as lauryl sulfate, sodium cetyl sulfate, glyceryl monostearate, diethylaminoethyl alkyl amide phosphate, isopropyl myristate, octyl alcohol, glyceryl and glycol esters of stearic acids; glycols such as propylene glycol, sorbitol; alcohols such as ethanol, isopropanol; higher fatty acids, such as stearic acid, palmitic acids; perfumes, essential oils; propellants such as halogenated hydrocarbons, e.g., dichlorodifluoromethane, trichlorofluoroethane, etc., carbon dioxide and nitrogen; solid diluents such as calcium carbonate, starch, bentonite, talc; and silicone-type fluids such as polysiloxane fluid. Selection of the particular carrier varies with use. Thus, higher fatty acids would be avoided in dermal preparations for the control of inflammatory skin conditions.

By employing the compounds in accordance with the present invention, the action of the microorganisms is somehow inhibited or altered.

Compositions and products which illustrate but do not limit the many forms in which the present invention may be employed for applying the amino acid compound to the situs of ammonia formation are presented in the following examples:

Example A

A disposable diaper is prepared having an absorbent core of comminuted wood pulp and a nonwoven porous cover. The upper surface of the wood pulp core has applied thereto 5.0 milligram of trisodium ethylenediaminetetraacetate per square inch of surface area. The trisodium ethylenediaminetetraacetate is applied to the absorbent core in a dry state from an aerosol spray employing dichlorodifluoromethane as a propellant after which the nonwoven cover is placed around the core.

Example B

A disposable diaper similar to that described in Example A except that both the upper surface of the wood pulp core and the fluid pervious cover has applied thereto trisodium ethylenediaminetetraacetate at a rate of 1.0 mg. per square inch of surface area.

Example C

A treated bed pad is prepared by applying a 20 percent aqueous solution of trisodium ethylenediaminetetraacetate to a web of cellulose fibers to impregnate the trisodium ethylenediaminetetraacetate and thereafter dried in air at temperatures of 60°C. to obtain cellulose fibers containing 0.5 gm. per square inch.

Example D

A baby lotion suitable for topical application is prepared by (1) heating Part A (below) to 70°C., (2) heating Part B (below) to 72°C (2) and (3) adding Part B to Part A and stirring until the mixture is cool.

| Part A | % Weight |
| --- | --- |
| Mineral oil | 35.00 |
| Lanolin | 1.00 |
| Cetyl alcohol | 1.00 |
| Silicone fluid 1000 cs | 5.00 |
| ARLACEL 80[1] | 2.10 |
| TWEEN 80[2] | 4.80 |
| Part B | |
| Water | 48.00 |
| Disodium salt of EDTA | 1.65 |
| Tetrasodium salt of EDTA | 1.35 |
| Sorbic acid | 0.10 |

[1]Sorbitan monoleate, a non-ionic, surface-active agent, product of Atlas Powder Company.
[2]Polyoxyethylene derivative of sorbitan monoleate, nonionic, surface-active agent, product of Atlas Powder Company.

Example E

A powder for topical application to the body is prepared by thoroughly mixing:

| | |
| --- | --- |
| Trisodium diethylenetriamine pentaacetic acid | 5 g |
| Starch | 305 g |
| Talc | 9690 g |

Example F

A body cream is prepared by (1) heating Part A (below) to 70° (2) Part B (below) to 75°C (3) adding Part B to Part A with agitation and (4) adjusting the pH to 5.5 with dilute sodium hydroxide.

| Part A | % Weight |
| --- | --- |
| Cetyl alcohol | 2.5 |
| Stearyl alcohol | 5.0 |
| Isopropyl myristate | 2.0 |
| Light silicone oil | 1.0 |
| "Emplex"[1] | 1.5 |
| Methyl paraben[2] | 0.15 |
| Propyl paraben[3] | 0.05 |
| Part B | |
| Deionized water | 78.8 |
| Disodium salt of EDTA | 4.0 |
| Propylene glycol | 5.0 |

[1]Sodium salt of reaction product of lactic and stearic acid (Patco Products, Kansas City, Missouri)
[2]Methyl hydroxybenzoate
[3]Propyl hydroxybenzoate

Example G

A lotion suitable as a body lotion may be prepared by (1) heating Part A (below) to 72°C., (2) Part B (below) to 75°C. (3) adding Part B to Part A with agitation and (4) adjusting the pH to 5.3 with dilute sodium hydroxide.

| Part A | % Weight |
| --- | --- |
| Cetyl alcohol | 1.9 |
| Stearyl alcohol | 3.0 |
| Isopropyl myristate | 1.3 |
| Light silicone oil | 0.8 |
| "Emplex" | 1.1 |
| Methyl paraben | 0.15 |
| Propyl paraben | 0.05 |
| Part B | |
| Deionized water | 81.7 |
| Propylene glycol | 3.0 |
| Disodium salt of EDTA | 7.0 |

Example H

An aerosol composition is prepared by first admixing the following materials in the indicated proportions:

| | Parts by Weight |
| --- | --- |
| Micropulverized talc | 2.50 |
| Na₃ EDTA | 2.50 |
| Fragrance | 0.16 |
| Anhydrous ethanol | 0.20 |
| Isopropyl myristate | 0.60 |

Thereafter, the mixture is placed in vessels suitable for pressurization (cans) and the following propellants added in the indicated proportions:

Freon 11[1]    47.02
Freon 12[2]    47.20

[1] Trichloromonofluoromethane (E.I. duPont de Nemours & Co.)
[2] Dichlorodifluoromethane (E.I. duPont de Nemours & Co.)

While previous methods of inhibiting ammonia production by microorganisms employed microbicidal methods, the present invention accomplishes the inhibition of ammonia production by microorganisms without kill of the organisms. Thus, when growth of Proteus mirabilis in heparinized blood at 37° with and without added disodium ethylenediaminetetraacetate was followed over a 24-hour period, there was found to be no detrimental effect on the growth of organisms as can be seen in the following table:

| Blood Inoculated with Proteus mirabilis | Bacterial Count | |
|---|---|---|
| | 0 Hours | 24 Hours |
| No Na$_2$EDTA | 100 × 10$^4$ | 182 × 10$^7$ |
| 2% Na$_2$EDTA | 100 × 10$^4$ | 231 × 10$^7$ |

What is claimed is:

1. A disposable diaper comprising a thin, waterproof backing sheet and a thin, moisture permeable facing sheet and an absorbent core disposed between said facing and said backing sheets, said diaper containing on at least the upper portions, including the surface area of the absorbent core or moisture permeable facing sheet first to intercept urine in use, a means for inhibiting ammonia formation therein including an aminopolycarboxylic acid compound in an amount of at least 0.001 gm. per square inch.

* * * * *